(12) United States Patent
Månsson et al.

(10) Patent No.: US 12,409,316 B2
(45) Date of Patent: *Sep. 9, 2025

(54) HEADSET FOR TRANSCRANIAL DIRECT-CURRENT STIMULATION, TDCS, AND A SYSTEM COMPRISING THE HEADSET

(71) Applicant: FLOW NEUROSCIENCE AB, Malmö (SE)

(72) Inventors: Daniel Månsson, Simrishamn (SE); Erik Rehn, Enebyberg (SE)

(73) Assignee: FLOW NEUROSCIENCE AB, Malmo (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/909,869

(22) Filed: Oct. 8, 2024

(65) Prior Publication Data

US 2025/0025683 A1    Jan. 23, 2025

Related U.S. Application Data

(63) Continuation of application No. 18/670,531, filed on May 21, 2024, now abandoned, which is a (Continued)

(51) Int. Cl.
*A61N 1/36* (2006.01)
*A61N 1/04* (2006.01)
*A61N 1/20* (2006.01)

(52) U.S. Cl.
CPC ......... *A61N 1/0456* (2013.01); *A61N 1/0484* (2013.01); *A61N 1/36025* (2013.01); *A61N 1/3603* (2017.08); *A61N 1/20* (2013.01)

(58) Field of Classification Search
CPC ................ A61N 1/0456; A61N 1/0484; A61N 1/36025; A61N 1/3603; A61N 1/20
See application file for complete search history.

(56) References Cited

U.S. PATENT DOCUMENTS

| 5,469,578 A | 11/1995 | Mattes |
| 7,976,451 B2 | 7/2011 | Zangen et al. |

(Continued)

FOREIGN PATENT DOCUMENTS

| BR | PI1100124 A2 | 4/2013 |
| CN | 1296854 A | 5/2001 |

(Continued)

OTHER PUBLICATIONS

Extended European Search Report for European Application No. EP23188609.4 dated Feb. 20, 2024, 4 pages.

(Continued)

*Primary Examiner* — James M Kish
*Assistant Examiner* — Natasha Patel
(74) *Attorney, Agent, or Firm* — COOLEY LLP

(57) ABSTRACT

A headset for transcranial brain stimulation including: a forehead frame defining an elongated arch; a first electrode arranged at a first end portion of the forehead frame; a second electrode arranged at a second end portion of the forehead frame; a bracket arranged at a center portion of the forehead frame; and a circuit comprising the first and second electrodes and configured to be powered according to a schedule for performing the transcranial brain stimulation.

31 Claims, 2 Drawing Sheets

Related U.S. Application Data continuation of application No. 16/480,678, filed as application No. PCT/EP2017/052251 on Feb. 2, 2017, now Pat. No. 12,017,062.

(56) References Cited

U.S. PATENT DOCUMENTS

| | | |
|---|---|---|
| 8,265,910 B2 | 9/2012 | Mishelevich et al. |
| 8,277,371 B2 | 10/2012 | Zangen et al. |
| 8,388,510 B2 | 3/2013 | Zangen et al. |
| 8,523,753 B2 | 9/2013 | Schneider et al. |
| 8,771,163 B2 | 7/2014 | Zangen et al. |
| 8,795,148 B2 | 8/2014 | Schneider et al. |
| 8,903,494 B2 | 12/2014 | Goldwasser et al. |
| 9,132,278 B2 | 9/2015 | Zangen et al. |
| 9,248,308 B2 | 2/2016 | Zangen et al. |
| 9,254,394 B2 | 2/2016 | Zangen et al. |
| 9,352,167 B2 | 5/2016 | Schneider |
| 9,370,658 B2 | 6/2016 | Neuvonen et al. |
| 9,440,070 B2 | 9/2016 | Goldwasser et al. |
| 9,492,679 B2 | 11/2016 | Schneider et al. |
| 9,533,168 B2 | 1/2017 | Zangen et al. |
| 9,636,517 B2 | 5/2017 | Pell et al. |
| 9,694,178 B2 | 7/2017 | Ruffini et al. |
| 9,782,602 B1 | 10/2017 | Lowin |
| 9,802,058 B2 | 10/2017 | Zangen et al. |
| 9,808,642 B2 | 11/2017 | Zangen et al. |
| 10,029,113 B2 | 7/2018 | Zangen et al. |
| 10,173,049 B2 | 1/2019 | Neuvonen et al. |
| 10,293,177 B2 | 5/2019 | Malchano et al. |
| 10,327,984 B2 | 6/2019 | Goodall et al. |
| 10,335,606 B2 | 7/2019 | Pell et al. |
| 10,537,703 B2 | 1/2020 | Tyler et al. |
| 10,576,279 B2 | 3/2020 | Muller et al. |
| 10,589,118 B2 | 3/2020 | Schneider |
| 10,625,091 B2 | 4/2020 | Zangen et al. |
| 10,814,131 B2 | 10/2020 | Goldwasser et al. |
| 10,918,855 B2 | 2/2021 | Eriksson et al. |
| 11,000,669 B2 | 5/2021 | Derungs |
| 11,033,731 B2 | 6/2021 | Jeffery et al. |
| 11,052,251 B2 | 7/2021 | Muller et al. |
| 11,207,540 B2 | 12/2021 | Zangen et al. |
| 11,241,584 B2 | 2/2022 | Pell et al. |
| 11,253,701 B2 | 2/2022 | Hagedorn |
| 11,324,963 B2 | 5/2022 | Etkin et al. |
| 11,351,362 B2 | 6/2022 | Månsson et al. |
| 11,400,289 B2 | 8/2022 | Alyagon et al. |
| 11,464,973 B2 | 10/2022 | Hagedorn |
| 11,577,090 B2 | 2/2023 | Etkin et al. |
| 2005/0197556 A1* | 9/2005 | Stoler ............... A61B 5/369 600/383 |
| 2009/0287108 A1 | 11/2009 | Levy |
| 2010/0057159 A1 | 3/2010 | Lozano |
| 2012/0163616 A1 | 6/2012 | Birch |
| 2013/0096363 A1 | 4/2013 | Schneider et al. |
| 2013/0317281 A1 | 11/2013 | Schneider et al. |
| 2014/0073996 A1 | 3/2014 | Jaguan |
| 2014/0200388 A1 | 7/2014 | Schneider et al. |
| 2014/0350431 A1 | 11/2014 | Hagedorn |
| 2015/0005840 A1 | 1/2015 | Pal et al. |
| 2015/0119689 A1 | 4/2015 | Pascual-Leone et al. |
| 2015/0181323 A1 | 6/2015 | Raklev |
| 2015/0190635 A1 | 7/2015 | Neuvonen et al. |
| 2015/0238762 A1 | 8/2015 | Pal et al. |
| 2015/0335875 A1 | 11/2015 | Goldwasser et al. |
| 2015/0335888 A1 | 11/2015 | Demers et al. |
| 2015/0351655 A1 | 12/2015 | Coleman |
| 2016/0008620 A1 | 1/2016 | Stubbeman |
| 2016/0008632 A1 | 1/2016 | Wetmore et al. |
| 2016/0023015 A1 | 1/2016 | Schneider et al. |
| 2016/0067516 A1 | 3/2016 | Schneider et al. |
| 2016/0074657 A1 | 3/2016 | Kwan et al. |
| 2016/0175589 A1 | 6/2016 | Wingeier |
| 2016/0317809 A1 | 11/2016 | Pal et al. |
| 2016/0360990 A1* | 12/2016 | Altshuler ............ A61B 5/6803 |
| 2017/0056642 A1 | 3/2017 | Moffitt et al. |
| 2017/0080234 A1 | 3/2017 | Gillespie et al. |
| 2017/0106203 A1 | 4/2017 | Schneider et al. |
| 2017/0113057 A1 | 4/2017 | Goodall et al. |
| 2017/0113058 A1 | 4/2017 | Schneider |
| 2017/0151430 A1 | 6/2017 | Neuvonen et al. |
| 2017/0165485 A1* | 6/2017 | Sullivan .............. A61B 5/0022 |
| 2017/0224978 A1* | 8/2017 | Lee ......................... A61N 1/04 |
| 2017/0224990 A1 | 8/2017 | Goldwasser et al. |
| 2017/0224991 A1 | 8/2017 | Wingeier et al. |
| 2017/0319852 A1 | 11/2017 | Wingeier et al. |
| 2017/0361094 A1 | 12/2017 | Cartledge et al. |
| 2017/0368297 A1 | 12/2017 | Tyler et al. |
| 2018/0133431 A1 | 5/2018 | Malchano et al. |
| 2018/0133504 A1 | 5/2018 | Malchano et al. |
| 2018/0236231 A1 | 8/2018 | Wingeier |
| 2019/0046794 A1 | 2/2019 | Goodall et al. |
| 2019/0113757 A1 | 4/2019 | Van Heugten |
| 2019/0159715 A1 | 5/2019 | Mishra Ramanathan et al. |
| 2019/0224481 A1 | 7/2019 | Wingeier |
| 2019/0232054 A1 | 8/2019 | Levenberg |
| 2020/0129119 A1 | 4/2020 | Ruffini et al. |
| 2020/0147340 A1 | 5/2020 | Tyler et al. |
| 2020/0175688 A1 | 6/2020 | Krummen et al. |
| 2020/0297999 A1 | 9/2020 | Pal |
| 2020/0302825 A1 | 9/2020 | Sachs et al. |
| 2021/0128905 A1 | 5/2021 | Månsson et al. |
| 2021/0162204 A1 | 6/2021 | Eriksson et al. |
| 2021/0169417 A1 | 6/2021 | Burton |
| 2021/0275801 A1 | 9/2021 | Månsson et al. |
| 2021/0299434 A1 | 9/2021 | Månsson et al. |
| 2021/0370047 A1 | 12/2021 | Rigaux |
| 2022/0096833 A1 | 3/2022 | Muller et al. |
| 2022/0280801 A1 | 9/2022 | Etkin et al. |
| 2022/0288409 A1 | 9/2022 | Järnefelt |
| 2022/0296903 A1 | 9/2022 | Maron-Katz et al. |
| 2023/0022546 A1 | 1/2023 | Malchano et al. |
| 2023/0082594 A1 | 3/2023 | Hagedorn |
| 2023/0104621 A1 | 4/2023 | Malchano et al. |
| 2023/0111776 A1 | 4/2023 | Malchano et al. |
| 2025/0025684 A1 | 1/2025 | Månsson et al. |

FOREIGN PATENT DOCUMENTS

| | | |
|---|---|---|
| CN | 105266802 A | 1/2016 |
| GB | 2521877 A | 7/2015 |
| GB | 2541947 A | 3/2017 |
| KR | 101628299 B1 | 6/2016 |
| KR | 20160095579 A | 8/2016 |
| WO | WO-2009137683 A2 | 11/2009 |
| WO | WO-2009137683 A3 | 2/2010 |
| WO | WO-2011123548 A2 | 10/2011 |
| WO | WO-2014082064 A1 | 5/2014 |
| WO | WO-2015184447 A1 | 12/2015 |
| WO | WO-2016017954 A1 | 2/2016 |
| WO | WO-2016042499 A1 | 3/2016 |
| WO | WO-2016179272 A1 | 11/2016 |
| WO | WO-2018141389 A1 | 8/2018 |
| WO | WO-2018141830 A1 | 8/2018 |
| WO | WO-2020025388 A1 | 2/2020 |
| WO | WO-2022027030 A1 | 2/2022 |

OTHER PUBLICATIONS

Final Office Action for U.S. Appl. No. 16/480,678 dated Dec. 14, 2021, 15 pages.

Final Office Action for U.S. Appl. No. 16/480,678 dated Nov. 2, 2022, 19 pages.

International Preliminary Report on Patentability mailed on Aug. 6, 2019 for PCT/EP2017/052251, 7 pages.

International Search Report and Written Opinion mailed on Oct. 26, 2017 for PCT/EP2017/052251, 10 pages.

Non-Final Office Action for U.S. Appl. No. 16/480,678 dated Jul. 20, 2021, 13 pages.

Non-Final Office Action for U.S. Appl. No. 16/480,678 dated May 27, 2022, 15 pages.

Non-Final Office Action for U.S. Appl. No. 18/909,870 mailed Dec. 13, 2024, 7 pages.

(56) References Cited

OTHER PUBLICATIONS

Office Action issued on Mar. 24, 2023 for Chinese Application No. 201780085021.X, with English translation, 11 pages.
Office Action issued on Oct. 27, 2022 for Chinese Application No. 201780085021.X, with English translation, 7 pages.
U.S. Appl. No. 18/670,531, filed May 21, 2024, by MÅnsson et al.

\* cited by examiner

HEADSET FOR TRANSCRANIAL DIRECT-CURRENT STIMULATION, TDCS, AND A SYSTEM COMPRISING THE HEADSET

CROSS-REFERENCE TO RELATED APPLICATION

This application is a Continuation Application of U.S. patent application Ser. No. 18/670,531, filed May 21, 2024, which is a Continuation Application of U.S. patent application Ser. No. 16/480,678, filed Jul. 25, 2019, now issued as U.S. Pat. No. 12,017,062, which is a U.S. National Stage Application under 35 U.S.C. § 371 of International Patent Application No. PCT/EP2017/052251, filed Feb. 2, 2017, the contents of each of which are incorporated herein by reference in their entireties.

TECHNICAL FIELD

The present invention relates to a headset for transcranial brain stimulation and a system comprising the headset.

BACKGROUND OF THE INVENTION

Transcranial brain stimulation, for example in the form of transcranial direct current stimulation, tDCS, which is a well-known technique for non-invasive neurostimulation of the brain. The transcranial brain stimulation is, e.g., used to help stroke recovery and patients with brain injuries and to treat depression. Transcranial brain stimulation uses external electrodes placed on the head of the patient, whereby the head of the patient together with the electrodes forms a closed circuit. A current, either direct or alternating, is applied to the circuit, which acts on the neurons of the brain. The placement of the electrodes can be done by a physician, but when transcranial brain stimulation is used to treat depression it should be performed so often that it is highly impractical for a physician to be present. The patient may be given the electrodes and instructions on how to place them, but this is of course error-prone. Another problem is patient compliance—the patient must apply the therapy often enough for it to have effect, but not too often as this may lead to unwanted side effects. The lack of presence of a physician when the therapy is self-performed also leads to a lack of patient feedback and monitoring.

SUMMARY OF THE INVENTION

In view of the above, an objective of the invention is to solve or at least reduce one or several of the drawbacks discussed above. Generally, the above objective is achieved by the attached independent patent claims.

According to a first aspect, the present invention is realized by a headset for transcranial brain stimulation, the headset comprising:
- a forehead frame, the forehead frame defining an elongated arch;
- a first electrode arranged at a first end portion of the forehead frame
- a second electrode arranged at a second end portion of the forehead frame;
- a bracket arranged at a center portion of the forehead frame; and
- a circuit comprising the first and second electrodes and being configured to be powered according to a schedule for performing the transcranial brain stimulation;

wherein upon use of the headset:
- the forehead frame is configured such that the first electrode is located at a left side of a forehead of a user of the headset, and such that the second electrode is located at a right side of the forehead of the user of the headset, and the bracket is configured to extend from the forehead frame over the skull of the user towards a neck portion of the user.

This provides a headset for performing transcranial brain stimulation wherein the electrodes are unlikely to be placed incorrectly on the forehead of the user. This has the advantage of allowing for transcranial brain stimulation to be performed without a physician available to place the electrodes on the head of the patient. Furthermore, the headset may be designed to be lightweight and comfortable, eliminating the need for fabric headwear which may be warm and uncomfortable when worn for extended periods of time. This further provides a comfortable headset which is impossible to mount such that the direction of the current is reversed, which may be critical in for example transcranial direct current stimulation, tDCS. During electrical transcranial brain stimulation, the potential of neuronal cells are influenced by an applied electric field. This field influences the neuronal cells under the stimulated area and pushes them closer or further away from their activation threshold.

The headset may further comprise:
- a memory configured to store the schedule for performing the transcranial brain stimulation;
- a controller configured to periodically power the circuit according to the schedule for performing the transcranial brain stimulation, thereby providing a current to the electrodes; and
- a power source configured to provide power to the circuit and the controller circuit.

Means for safer transcranial brain stimulation are hence provided. Further the need for involvement of a physician upon performing the transcranial brain stimulation is reduced.

The memory may further be configured to store information pertaining to performed transcranial brain stimulation. Hence, means for monitoring the patient's progress through the therapy is provided. This further reduces the need for involvement of a physician upon performing the transcranial brain stimulation.

The controller may further be configured to remind the user to use the headset according to the schedule for performing the transcranial brain stimulation. Counteracting negligence or unwitting non-compliance, e.g. due to misunderstanding or miscommunication, in relation to the therapy on account of the patient is provided.

The first and second electrodes may be pivotable such that they can adapt to the shape of the forehead of the user. A more comfortable headset which is adaptable to many different shapes of patient foreheads and reduces the need for size adaptability of the headset is provided.

The first and second electrodes may comprise an adhesive layer configured such that it adheres to the forehead of the user. Ensuring that the headset does not drift during use, securing it in place on the head of the patient is provided.

In a second aspect, the current invention also relates to a system comprising a headset for transcranial brain stimulation and a non-transitory computer-readable recording medium having recorded thereon a program which is executable on an electronic device having processing capabilities, wherein the headset comprises:
- a forehead frame, the forehead frame defining an elongated arch;

a first electrode arranged at a first end portion of the forehead frame;

a second electrode arranged at a second end portion of the forehead frame;

a bracket arranged at a center portion of the forehead frame;

a circuit comprising the first and second electrodes and being configured to be powered according to a schedule for performing the transcranial brain stimulation; and wherein upon use of the headset:

the forehead frame is configured such that the first electrode is located at a left side of a forehead of a user of the headset, and such that the second electrode is located at a right side of the forehead of the user of the headset, and the bracket is configured to extend from the forehead frame over the skull of the user towards a neck portion of the user, wherein the program comprises program code portions which when executed on the electronic device is configured to:

store the schedule for performing the transcranial brain stimulation in a computer memory; and control the electronic device to send a control signal to the headset such that transcranial brain stimulation is performed according to the schedule for performing the transcranial brain stimulation.

This provides the possibility for a user to perform a transcranial brain stimulation therapeutic schedule themselves with the aid of an electronic device, further limiting the need for visits to or by a physician.

The headset may further comprise:

a transceiver configured to communicate with the electronic device;

a controller configured to control the first and second electrodes according to the control signal; and a power source configured to provide power to the circuit and the controller circuit.

This provides a system where the headset does not need to be wired to any external circuitry or power supply, improving portability of the headset and increasing user comfort and convenience.

The program may further comprise program code portions which when executed on the electronic device is configured to remind the user to use the headset according to the schedule for performing the transcranial brain stimulation. This provides a system for performing transcranial brain stimulation where the user can be conveniently prompted to wear the headset and signaled when to remove it. This provides a safety measure against over-use of the headset by the user due to negligence or ignorance.

The program may further comprise program code portions which when executed on the electronic device is configured to display information on a display of the electronic device in accordance with a schedule for displaying the information, wherein the schedule for displaying information is related to the schedule for performing the transcranial brain stimulation.

The program may further comprise program code portions which when executed on the electronic device is configured to prompt the user to input information pertaining to status of the user.

The program may further comprise program code portions which when executed on the electronic device is configured to update the schedule for performing the transcranial brain stimulation.

The program may further comprise program code portions which when executed on the electronic device is configured to store information pertaining to performed transcranial brain stimulation on a computer memory.

The electronic device may be a handheld electronic device.

The program may be an application downloadable to the electronic device via an application providing service.

The above mentioned features of the method, when applicable, apply to this second aspect as well. In order to avoid undue repetition, reference is made to the above.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTION OF THE DRAWINGS

The above and other aspects of the present invention will now be described in more detail, with reference to appended drawings showing embodiments of the invention. The figures should not be considered limiting the invention to the specific embodiment; instead they are used for explaining and understanding the invention.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION OF THE INVENTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
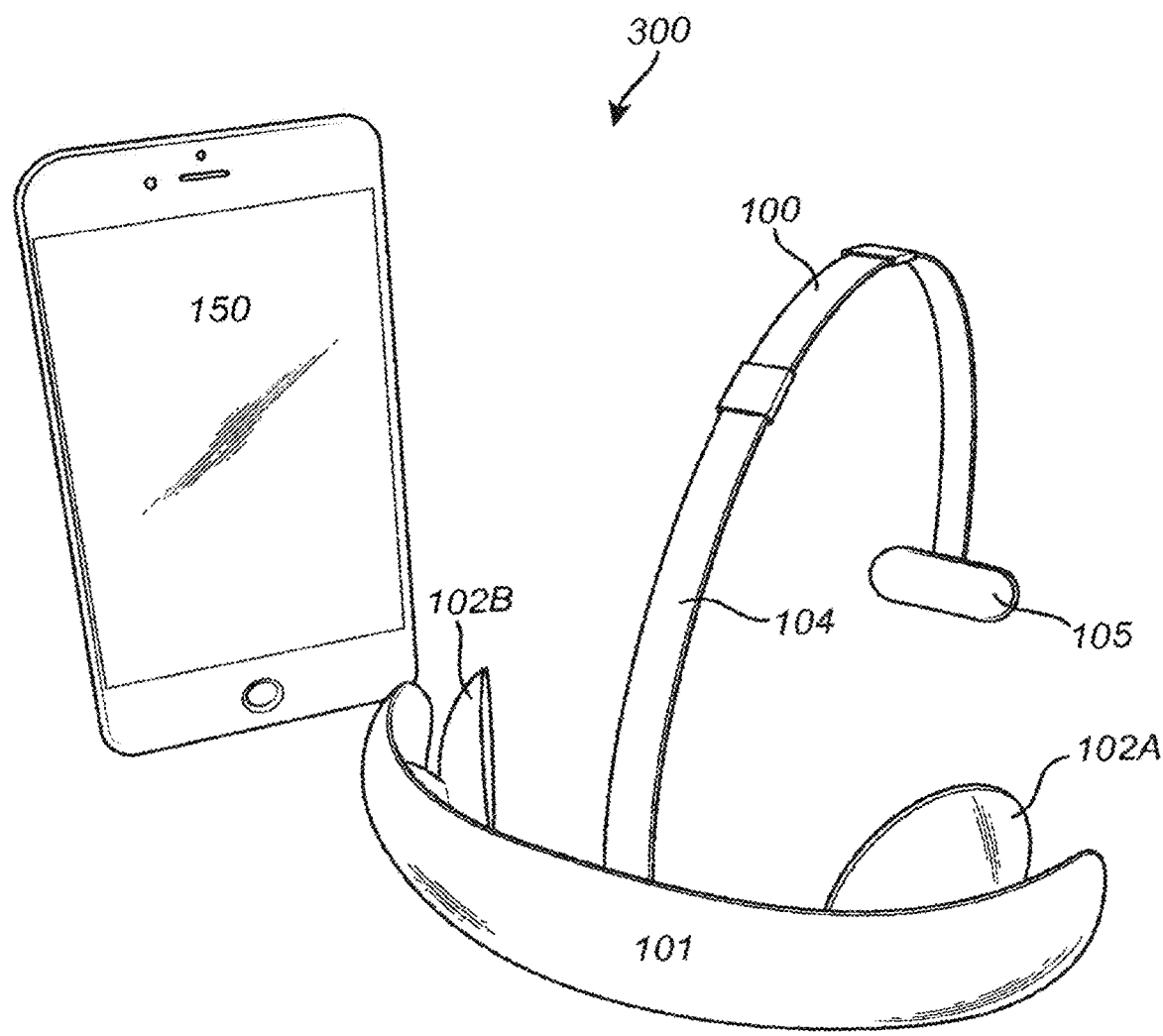
FIG. 1 illustrates a system comprising a headset for transcranial brain stimulation and an electronic device configured to control the headset.

In FIG. 1, a view of the headset 100 for transcranial brain stimulation is disclosed. The headset 100 comprises a forehead frame 101, a first and second electrodes 102A, 102B and a bracket 104.

The shape of the forehead frame 101 is designed to fit a forehead of a user of the headset 100. The forehead frame 101 is defining an elongated arch. This allows the forehead frame 101 to follow approximately the shape of the forehead of the user when placed on the head. The forehead frame 101 may be manufactured by e.g. plastic, composite materials, metal or any other suitable material. The forehead frame 101 is configured to support the first and second electrodes 102A, 102B. The forehead frame 101 is configured to support the bracket 104. The first electrode 102A is arranged at a first end portion of the forehead frame 101. The second electrode 102B is arranged at a second end portion of the forehead frame 101. Hence, the first and second electrodes 102A, 102B are placed on the forehead frame 101 such that when the forehead frame 101 is worn by the user, the first and second electrodes 102A, 102B will come in contact with the forehead on either side of the user's head.

The first and second electrodes 102A, 102B may be configured to pivot to some degree. Thus, a headset 100 is provided where the major surface of each electrode 102A, 102B is pivoted to be principally parallel to the surface of the forehead of the user. The first and second electrodes 102A, 102B need not be configured to pivot.

The first and second electrodes 102A, 102B may be of any type of conducting material suitable for repeated use. Alternatively, the first and second electrodes 102A, 102B may be configured for one-time use only, in which case they are to be replaced by the user between uses.

The first and second electrodes 102A, 102B may comprise an adhesive layer. The adhesive layer may be discarded after use. The adhesive layer ensures proper contact between the electrode and the forehead of the user while also providing a hygienic solution.

The headset 100 may of course be provided with further electrodes, in case the desired scheme for transcranial brain stimulation so requires.

For some schemes of transcranial brain stimulation, the first and second electrodes 102A, 1028 correspond to a first and second side of the user's forehead, respectively. By this is meant that each electrode 102A, 102B is configured to be brought into contact only with either the left or the right side of the user's forehead.

The bracket 114 is arranged at a center portion of the forehead frame 101. The bracket 104 may be arranged to the forehead frame 101 in any suitable way. For example, the bracket 104 may be screwed, glued or fastened in any other suitable way to the fore head frame 101. In this context the phrase "center portion" should be understood to refer to any part of the longitudinal extension of the forehead frame 101 which lies between the first and second electrodes 102A, 102B. The bracket 104 has a longitudinal extension which, when the headset 100 is used, extends from the forehead of the user towards the back of the user's head. In this way, the bracket 104 ensures that the user wears the headset 100 such that the first and second electrodes 102A, 102B come in contact only with their respective side of the user's forehead. The bracket 104 may be constructed such that its extension from the frame is variable, ensuring a better fit for the user. This can be achieved in many ways, which the skilled person understands. Alternatively, the bracket 104 may be of fixed length. The bracket 104 may further comprise a support cushion 105 arranged at an end portion of the bracket 104 being opposite to where the bracket 104 is arranged at the forehead frame 101. The cushion 105 makes the bracket 104 more comfortable for the user.

Figure 2:
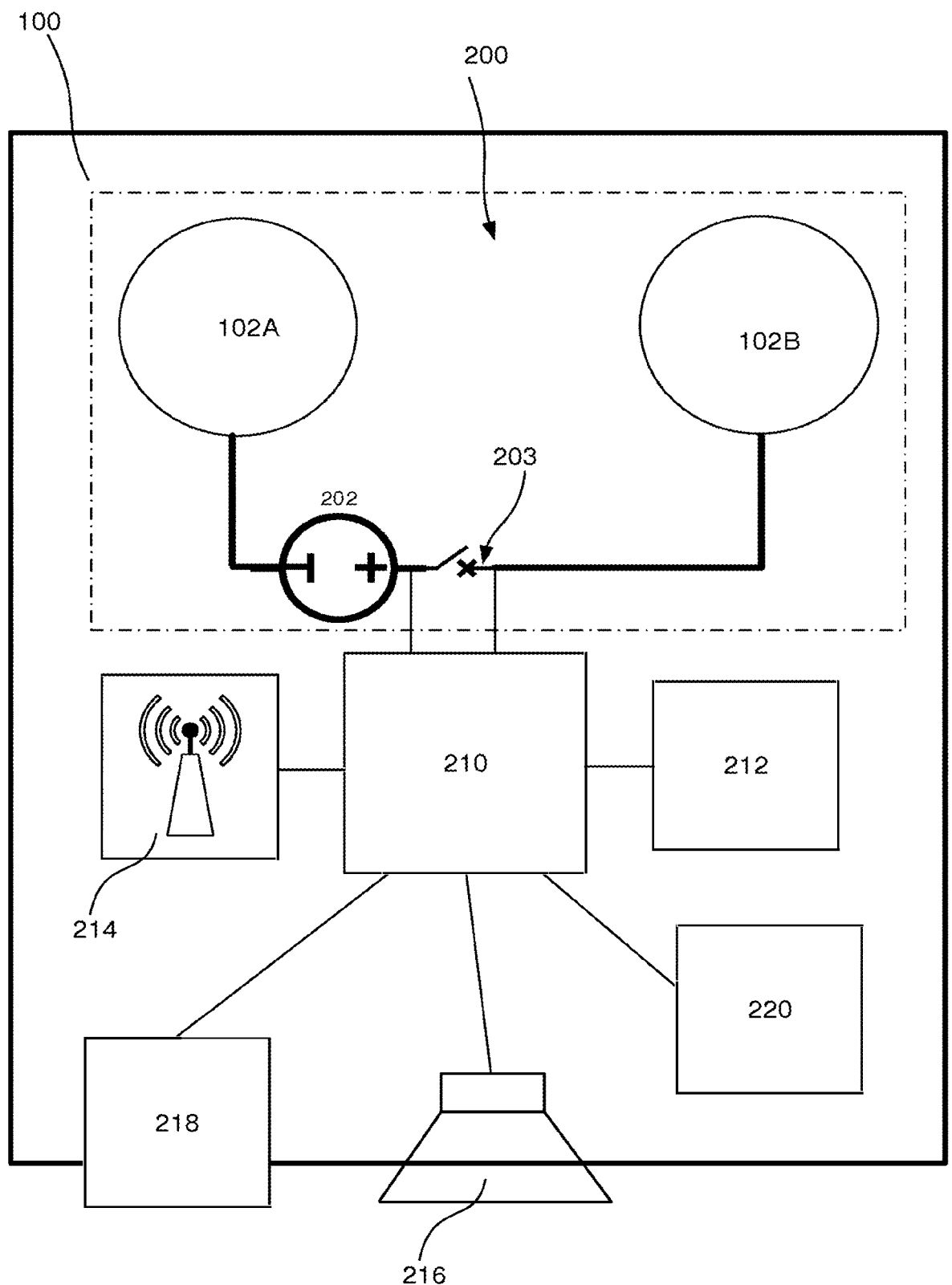
FIG. 2 is a schematic sketch of a headset for transcranial brain stimulation.

The first and second electrodes 102A, 102B are further comprised in a circuit 200. The circuit 200 will now be further described in connection with FIG. 2. The circuit 200 is configured to be powered according to a schedule for performing transcranial brain stimulation.

The first and second electrodes 102A, 102B are connected in the circuit 200. The circuit 200 further comprises a power source 202 and a switch 203. Upon the headset 100 being worn by the user and upon the switch 203 is engaged, a closed circuit comprising the first and second electrodes 102A, 102B, the user's forehead and the power source 202 is formed. This allows current to flow through the user's cranium. The power source 202 may be a battery.

The headset 100 may further comprise a controller 210. The controller 210 is configured to periodically power the circuit 200 according to a schedule for performing transcranial brain stimulation. Thereby a current is periodically provided to user's brain for performing the transcranial brain stimulation. The controller 210 is configured to periodically control the switch 203. The controller 210 may be hardware or software implemented. The controller 210 may comprise a microcontroller, a system of microcontrollers, or any type of processor or control circuit which can engage and disengage the switch 202. This provides a headset 100 which may vary the electric impulses to the head of the user according to schemes for transcranial brain stimulation.

The headset 100 may further comprise a memory 212. The memory may be any type of non-volatile memory configured to store digital data. The memory 212 may, e.g., be a ROM, a solid state drive, a flash memory or any other device which can persistently store digital information. The memory 212 may, e.g., be configured to store a schedule for performing the transcranial brain stimulation. The schedule for performing the transcranial brain stimulation may comprise information pertaining to when to open and close the switch 203. The schedule for performing the transcranial brain stimulation may comprise information pertaining to when the user shall wear the headset and for what duration in order to receive the transcranial brain stimulation. The controller 210 may be arranged to read data from the memory 212. Hence, the controller 210 may be configured to receive information from the memory 212 on the schedule for performing the transcranial brain stimulation. However, it is realized that the schedule for transcranial brain stimulation may be stored elsewhere in some other memory accessible by the controller 210. This will be discussed in more detail below. The controller 210 may further be configured to write data to the memory 212. Hence, the controller 210 may be configured to write data to the memory pertaining to performed transcranial brain stimulation.

The schedule for performing the transcranial brain stimulation may comprise information pertaining to when to open and close the switch 203. The schedule for performing the transcranial brain stimulation may comprise information pertaining to when the user shall wear the headset 100 and for what duration in order to receive the transcranial brain stimulation. The controller 210 may be arranged to read data from the memory 212. Hence, the controller 210 may be configured to receive information from the memory 212 on the schedule for performing the transcranial brain stimulation. However, it is realized that the schedule for transcranial brain stimulation may be stored elsewhere in some other memory accessible by the controller 210. This will be discussed in more detail below. The controller 210 may further be configured to write data to the memory 212. Hence, the controller 210 may be configured to write data to the memory pertaining to performed transcranial brain stimulation.

The headset 100 may further be configured to signal when the user shall wear or take off the headset 100 for receiving the transcranial brain stimulation. This can be done in many different ways. For this purpose, the headset 100 may comprise a speaker 216. The controller 210 may be configured to control the speaker 216. The speaker 216 is configured to emit sound pertaining to information reminding the user to wear or remove the headset 100. Some non-limiting examples of sounds are beeping sounds and voice synthesis. The loudspeaker 216 may be arranged in the forehead frame 101. The headset 100 may comprise a light source 218. The light source 218 may e.g. comprise one or more LED: s. The controller 210 may be configured to control the light source 218. The light source 218 is configured to emit light pertaining to information reminding the user to wear or remove the headset 100. For example, the light source 218 may be configured to emit light having different colors for reminding the user to wear or remove the headset 100. The light source 218 may be configured to emit light pulses of different frequency to remind the user. The light source 218 may be arranged in the forehead frame 101. The headset may comprise a vibrator 220. The controller 210 may be configured to control the vibrator 220. The vibrator 220 is configured to emit vibrate in order to remind the user to wear or remove the headset 100. The vibrator may be arranged in the forehead frame 101. Any combination of the loudspeaker 216, the light source 218 or the vibrator 220 may be used for reminding the user to wear or remove the headset 100. Hence, just one of them, two of them, or all of them may be used for reminding the user to wear or remove the headset 100.

The headset 100 may be included in a system 300 for transcranial brain stimulation. As illustrated in FIG. 1 the system 300 comprises the headset 100 as described above and an electronic device 150. The electronic device 150 having processing capabilities and is configured to execute a computer program. The electronic device may e.g. be a handheld electronic device, such as a laptop, a smartphone, or a smartwatch. In order to communicate with the electronic device 150, the headset 100 may further comprise a transceiver 214, see FIG. 2. The transceiver 214 is a wireless transceiver configured to communicate over a suitable wireless protocol, such as Bluetooth, Wi-Fi, ZigBee, or wireless USB. Hence, the transceiver 214 is used to communicate with the electronic device 214.

The computer program may be an application downloadable to the electronic device via an application providing service. The computer program comprises code portions which when executed on the electronic device 150 is configured to perform different acts.

A code portion of the computer program is configured to store the schedule for performing the transcranial brain stimulation in a computer memory. The computer memory may be the memory 212 of the headset 100. Alternatively, the computer memory may be a memory of the electronic device. Yet alternatively, the computer memory may be a memory of a server (not shown), the electronic device 150 being connected to the server. Yet alternatively, the computer memory may comprise one or more of the above mentioned memories. Hence, different portions of the schedule may be stored on different memories. Hence, the storing of the schedule may be distributed over a plurality of memories.

A code portion of the computer program is configured to control the electronic device 150 to send a control signal to the controller 210 of the headset 100. The control signal comprising information pertain to how to control the switch 203 for performing the transcranial brain stimulation.

A code portion of the computer program may further be configured to remind the user to use the headset according to the schedule for performing the transcranial brain stimulation. The reminder may be prompted to the user using one or more of the loudspeaker 216, the light source 218 and the vibrator 220 of the headset. Alternatively or in combination, the reminder may be prompted to the user using one or more of a loudspeaker of the electronic device, a light source of the electronic device, a vibrator of the electronic device and a display of the electronic device. For example, the user may be prompted by a message displayed on the display of the electronic device.

A code portion of the computer program may further be configured to display information on the display of the electronic device in accordance with a schedule for displaying information. The schedule for displaying information may related to the schedule for performing the transcranial brain stimulation. The displayed information may e.g. be a video sequence to be watched in connection with receiving the transcranial brain stimulation. The video sequence may be video lesson being part of a treatment program. The video sequence may be an instructions video instructing the user how to put on and use the headset 100.

A code portion of the computer program may further be configured to prompt the user to input information pertaining to status of the user. The user may be prompted by displaying a message on the display of the electronic device 150. The input information prompted for may be information pertaining to information about the user's current health. The user may input such information through input means of the electronic device. An example of an input means is a keyboard (virtual on a touch screen or realized as mechanical buttons). The input information may then be stored in the computer memory. The input information may then be provided to a physician for reviewing the schedule for the transcranial brain stimulation of the user.

A code portion of the computer program may further be configured to store information pertaining to performed transcranial brain stimulation in the computer memory. The information pertaining to performed transcranial brain stimulation may then be provided to a physician for reviewing the schedule for the transcranial brain stimulation of the user.

By being provided with the input information and the information pertaining to performed transcranial brain stimulation the physician is provided with the possibility to assess the progress of the user and to immediately make any adjustments required to the user's schedule for transcranial brain stimulation as well as inform the user that such adjustments have been made.

A code portion of the computer program may further be configured to update the schedule for performing the transcranial brain stimulation. This gives the possibility for e.g. the physician to adjust the schedule for transcranial brain stimulation.

The person skilled in the art realizes that the present invention by no means is limited to the preferred embodiments described above. On the contrary, many modifications and variations are possible within the scope of the appended claims.

As described above, the headset comprises a transceiver. This provides the possibility for the headset to communicate wirelessly with the electronic device over a network protocol such as Bluetooth or Wi-Fi. The skilled person understands that any network protocol capable of transmitting digitally represented data is possible to use.

The system may, through the electronic device, also provide the user with information about the transcranial brain stimulation progress such as logs of their use, changes to their schedule recommended by the physician, status of the headset regarding e.g. battery charge state or malfunctions, or any other information.

As shown through this description, a headset and system for transcranial brain stimulation is provided which allows a user to autonomously and conveniently perform steps of such treatment which previously required visits to or by a physician.

Additionally, variations to the disclosed embodiments can be understood and effected by the skilled person in practicing the claimed invention, from a study of the drawings, the disclosure, and the appended claims.

The invention claimed is:

1. A headset, comprising:
a frame configured to fit across a forehead of a user;
a first electrode coupled to the frame at a first end portion of the frame such that the first electrode is configured to be disposed on a first side of the forehead when the frame is fitted across the forehead;
a second electrode coupled to the frame at a second end portion of the frame such that the second electrode is configured to be disposed on a second side of the forehead when the frame is fitted across the forehead, the first and second electrodes collectively configured to provide a scheme for transcranial stimulation to the user when in contact with the first and second sides of the forehead;
a bracket coupled to a center portion of the frame, the bracket configured to extend from the frame, over a top of a head of the user, and to a back of the head when the frame is fitted across the forehead, the bracket configured to support the frame when fitted across the forehead to ensure that the first and second electrodes only come in contact with their respective sides of the forehead such that current flows in a predetermined direction between the first and second electrodes; and
a processor operatively coupled to the first and second electrodes, the processor configured to control the first and second electrodes to deliver current through a brain of the user in the predetermined direction to provide the scheme for the transcranial stimulation.

2. The headset of claim 1, wherein the bracket extends from the frame in a manner that prevents the frame from being fitted in a different orientation across the forehead of the user such that the current delivered by the first and second electrodes remains in the predetermined direction.

3. The headset of claim 1, wherein the bracket includes a longitudinal extension that is coupled to a support structure having a wider profile than the longitudinal extension.

4. The headset of claim 3, wherein the support structure is configured to rest on a back of the head when the frame is fitted across the forehead.

5. The headset of claim 4, wherein the support structure is a support cushion.

6. The headset of claim 1, wherein the frame, when fitted across the forehead of the user, terminates at the first and second sides of the forehead.

7. The headset of claim 1, wherein the first and second electrodes are pivotable relative to the frame such that, when the frame is fitted across the forehead of the user, a surface of the first electrode can be parallel to the first side of the forehead of the user and a surface of the second electrode can be parallel to the second side of the forehead of the user.

8. The headset of claim 1, wherein each of the first electrode and the second electrode includes an adhesive layer that is configured to adhere to a surface of the forehead.

9. The headset of claim 8, wherein the adhesive layers of the first and second electrodes are removable from the first and second electrodes such that the adhesive layers can be discarded after use.

10. The headset of claim 1, wherein the bracket is configured to be adjustable in length such that the bracket can be fitted around different sizes of heads of users.

11. The headset of claim 1, further comprising:
a memory configured to store a schedule for performing the transcranial stimulation,
the processor configured to control the first and second electrodes to deliver the current based on the schedule.

12. A headset, comprising:
a frame defining an elongated arch sized to fit across a forehead of a user;
a first electrode disposed at a first end portion of the frame;
a second electrode disposed at a second end portion of the frame; and
a longitudinal extension having a first end coupled to a center portion of the frame and a second end that terminates in a support structure configured to contact a back of a head of the user,
the longitudinal extension mountable on the head to support the frame in a configuration extends across the forehead of the user and places the first electrode in coupling with a left side of the forehead and the second electrode in coupling with a right side of the forehead to deliver current in a predetermined direction without being mountable on the head to support the frame in a different configuration that reverses the predetermined direction of the current,
the first electrode and the second electrodes configured to form part of a closed circuit that is configured to deliver the current in the predetermined direction to provide transcranial stimulation to the user when in coupling with the left and right sides of the forehead, respectively.

13. The headset of claim 12, wherein the first and second electrodes are pivotable relative to the frame such that, when the frame is supported on the head, a surface of the first electrode can be parallel to the left side of the forehead of the user and a surface of the second electrode can be parallel to the right side of the forehead of the user.

14. The headset of claim 12, wherein each of the first electrode and the second electrode includes an adhesive layer that is configured to adhere to a surface of the forehead.

15. The headset of claim 14, wherein the adhesive layers of the first and second electrodes are removable from the first and second electrodes such that the adhesive layers can be discarded after use.

16. The headset of claim 12, wherein the longitudinal extension is configured to be adjustable in length such that the longitudinal extension can be fitted around different sizes of heads of users.

17. The headset of claim 12, wherein the longitudinal extension has a width that is less than a width of the frame.

18. The headset of claim 13, wherein the first and second electrodes are disposed on structures coupled to the frame that have a lateral dimension that is greater than a width of the frame.

19. The headset of claim 12, further comprising:
a memory configured to store a schedule for performing the transcranial stimulation; and a processor coupled to the memory, the circuit, and the first and second electrodes, the processor configured to control the circuit such that the first and second electrodes deliver current based on the schedule to provide the transcranial stimulation.

20. The headset of claim 12, wherein the support structure has a wider profile than the longitudinal extension.

21. The headset of claim 13, wherein the frame, when fitted across the forehead of the user, terminates at the right and left sides of the forehead.

22. The headset of claim 12, wherein the closed circuit via the first electrode and the second electrode is configured to deliver the current from the second electrode on the right side of the forehead, through a portion of the head of the user, and to the first electrode on the left side of the forehead.

23. A headset, comprising:
a frame;
a first electrode disposed at a first end portion of the frame;
a second electrode disposed at a second end portion of the frame, the frame configured to be worn on a forehead of a user such that the first and second electrodes are in coupling with first and second sides of the forehead and are configured to deliver current in a predetermined direction to the user to provide transcranial stimulation;
a longitudinal extension having a first end coupled to a center portion of the frame and a second end extending away from the frame, the longitudinal extension being shaped to extend over a head of the user such that the longitudinal extension prevents the frame from being worn in an orientation in which a direction of current delivered by the first and second electrodes is reversed due to the first and second electrodes being placed incorrectly on the forehead; and a processor operatively coupled to the first and second electrodes, the processor configured to activate the first and second electrodes such that the first and second electrodes deliver the current in the predetermined direction.

24. The headset of claim 23, wherein the second end of the longitudinal extension is coupled to a support structure having a wider profile than the longitudinal extension.

25. The headset of claim 24, wherein the support structure is a support pad.

26. The headset of claim 24, wherein the support structure is configured to rest on a back of the head when the frame is worn on the forehead.

27. The headset of claim 23, wherein the first and second sides of the forehead are left and right sides of the forehead, and the frame terminates at the left and right sides of the forehead when worn on the forehead.

28. The headset of claim 23, wherein the first and second electrodes are pivotable relative to the frame such that, when the frame is fitted across the forehead of the user, a surface of the first electrode can be parallel to the first side of the forehead of the user and a surface of the second electrode can be parallel to the second side of the forehead of the user.

29. The headset of claim 23, wherein each of the first electrode and the second electrode includes an adhesive layer that is configured to adhere to a surface of the forehead.

30. The headset of claim 29, wherein the adhesive layers of the first and second electrodes are removable from the first and second electrodes such that the adhesive layers can be discarded after use.

31. The headset of claim 23, wherein the longitudinal extension is configured to be adjustable in length such that the longitudinal extension can be fitted around different sizes of heads of users.

* * * * *

UNITED STATES PATENT AND TRADEMARK OFFICE
CERTIFICATE OF CORRECTION

PATENT NO. : 12,409,316 B2
APPLICATION NO. : 18/909869
DATED : September 9, 2025
INVENTOR(S) : Daniel Månsson et al.

Page 1 of 1

It is certified that error appears in the above-identified patent and that said Letters Patent is hereby corrected as shown below:

In the Claims

<u>Claim 12:</u>
Column 10, Line 28:
"support the frame in a configuration extends across the"
Should read:
-- support the frame in a configuration that extends across the --

<u>Claim 12:</u>
Column 10, Line 36:
"the first electrode and the second electrodes configured to"
Should read:
-- the first electrode and the second electrode configured to --

Signed and Sealed this
Ninth Day of December, 2025

John A. Squires
*Director of the United States Patent and Trademark Office*